US00PP26642P2

(12) United States Plant Patent
Thompson

(10) Patent No.: US PP26,642 P2
(45) Date of Patent: Apr. 26, 2016

(54) JAPANESE HASKAP PLANT NAMED 'KEIKO'

(50) Latin Name: ***Lonicera caerulea* ssp. *emphyllocalyx***
Varietal Denomination: Keiko

(71) Applicant: Maxine M. Thompson, Corvallis, OR (US)

(72) Inventor: Maxine M. Thompson, Corvallis, OR (US)

(73) Assignee: MAXINE M. THOMPSON TRUST, Corvallis, OR (US)

( * ) Notice: Subject to any disclaimer, the term of this patent is extended or adjusted under 35 U.S.C. 154(b) by 111 days.

(21) Appl. No.: 14/121,242

(22) Filed: Aug. 14, 2014

(51) Int. Cl.
*A01H 5/00* (2006.01)

(52) U.S. Cl.
USPC ..... Plt./156

(58) Field of Classification Search
USPC ..... Plt./156
See application file for complete search history.

*Primary Examiner* — Annette Para
(74) *Attorney, Agent, or Firm* — Penny J. Aguirre

(57) ABSTRACT

A new cultivar of Japanese haskap plant, 'Keiko', that is characterized by its upright and spreading plant habit, its vigorous growth habit, its high fruit yields, its frost tolerant flowers, its fruits that are medium large in size, oval in shape, medium firmness, produce little juice, good sweet and tart tasting, and maintain their appearance, firmness and taste for at least 4 weeks in cold storage at 33° F. to 35° F., and its little or no disease or pest problems requiring no chemicals for desirable fruit production.

2 Drawing Sheets

Botanical classification: *Lonicera caerulea* ssp. *emphyllocalyx*.

Variety denomination: 'Keiko'.

CROSS REFERENCE TO RELATED APPLICATIONS

This application is co-pending with U.S. Plant Patent Applications filed for 3 plants derived from the same breeding program that are entitled Japanese haskap Plant Named 'Taka' (U.S. Plant patent application Ser. No. 14/121,242), Japanese haskap Plant Named 'Tana' (U.S. Plant patent application Ser. No. 14/121,254), and Japanese haskap Plant Named 'Kapu' (U.S. Plant patent application Ser. No. 14/121,252).

BACKGROUND OF THE INVENTION

The present invention relates to a new and distinct cultivar of *Lonicera caerulea* ssp. *emphyllocalyx* and will be referred to hereafter by its cultivar name, 'Keiko'. 'Keiko' is a new cultivar of Japanese blue honeysuckle berry, also known as Japanese haskap, a plant grown for its fruit that is marketed as fresh and frozen fruit and processed food products.

The new Invention arose from an ongoing controlled breeding program that initiated in 2001 in Corvallis, Oreg. with the planting of seeds collected in 2000 from several berry farms in Hokkaido, Japan. The objectives of the breeding program are to develop superior cultivars of this early ripening berry plant that could be grown in moderate to colder climates combined with an upright spreading plant habit and fruit that were large in size, firm, easy to pick, good tasting, and with a high yield rate.

This new Japanese haskap cultivar, 'Keiko', arose from seed collected from open pollination of an unnamed Japanese haskap plant designated as "selection #8" that was growing on a farm in Bibai, Japan. 'Keiko' was selected in Corvallis, Oreg. as a single unique plant (selection #22-26) in 2004 from the population of resulting seedlings.

Asexual propagation of the new cultivar was first accomplished by the Inventor by hardwood stem cuttings in 2004 in Corvallis, Oreg. Asexual propagation by hardwood and softwood cuttings has determined that the characteristics of the new cultivar are stable and are reproduced true to type in successive generations.

SUMMARY OF THE INVENTION

The following traits have been repeatedly observed and represent the characteristics of the new cultivar as grown outdoors in a trial plot for eight years in Corvallis, Oreg. These attributes in combination distinguish 'Keiko' as a unique cultivar of haskap.

1. 'Keiko' exhibits an upright and spreading plant habit.
2. 'Keiko' exhibits a vigorous growth habit.
3. 'Keiko' exhibits very high fruit yields.
4. 'Keiko' exhibits frost tolerant flowers and can be grown in regions prone to spring frosts.
5. 'Keiko' exhibits fruits that are medium large in size, oval in shape, medium firmness, good sweet/tart tasting and produce little juice.
6. 'Keiko' exhibits fruit that maintain their appearance, firmness and taste for at least 4 weeks in cold storage at 33° F. to 35° F.
7. 'Keiko' produces fruit in early to mid June in Oregon.
8. 'Keiko' has shown little or no disease or pest problems and requires no chemicals for desirable fruit production.

The Inventor has no records on the characteristics of the female parent, selection #8. 'Keiko' can be most closely compared to the cultivar 'Yufutsu' (not patented) and to cultivars from the same breeding program; 'Kapu', 'Taka', and 'Tana'. 'Yufutsu' differs from 'Keiko' in having a denser and low spreading plant habit (wider than tall) and in having berries that are smaller, oblong in shape, less firm, and more juicy with a lower BRIX. 'Kapu' differs from 'Keiko' in having a more upright plant habit and fruit that is oval-ovate in shape, and slightly less juicy and firmer. 'Taka' differs from 'Keiko' in having fruit that is cylindrical in shape and a slighter higher BRIX level. 'Tana' differs from 'Keiko' in having a greater number of basal shoots and berries with a rounded apex. 'Keiko' can also be compared to typical plants of related Russian honeyberries; *Lonicera caerulea* ssp. *edulis* and *Lonicera caerulea* ssp. *kamtchatica*. One of the main differences is that these species are adapted only to regions with very cold winters, whereas Japanese haskap thrive in milder climates as well as in colder climates. In Oregon, Russian honeyberries bloom about one month before Japanese haskap, before there are bees out for pollination and consequently have low or no fruit yields.

BRIEF DESCRIPTION OF THE DRAWINGS

The accompanying colored photographs were taken in mid summer and illustrate the overall appearance and distinct characteristics of 9 year-old plants of the new Japanese haskap as grown in a trial garden in Corvallis, Oreg.

The photograph in FIG. 1 provides a view of the plant habit of 'Keiko'.

Figure 1:
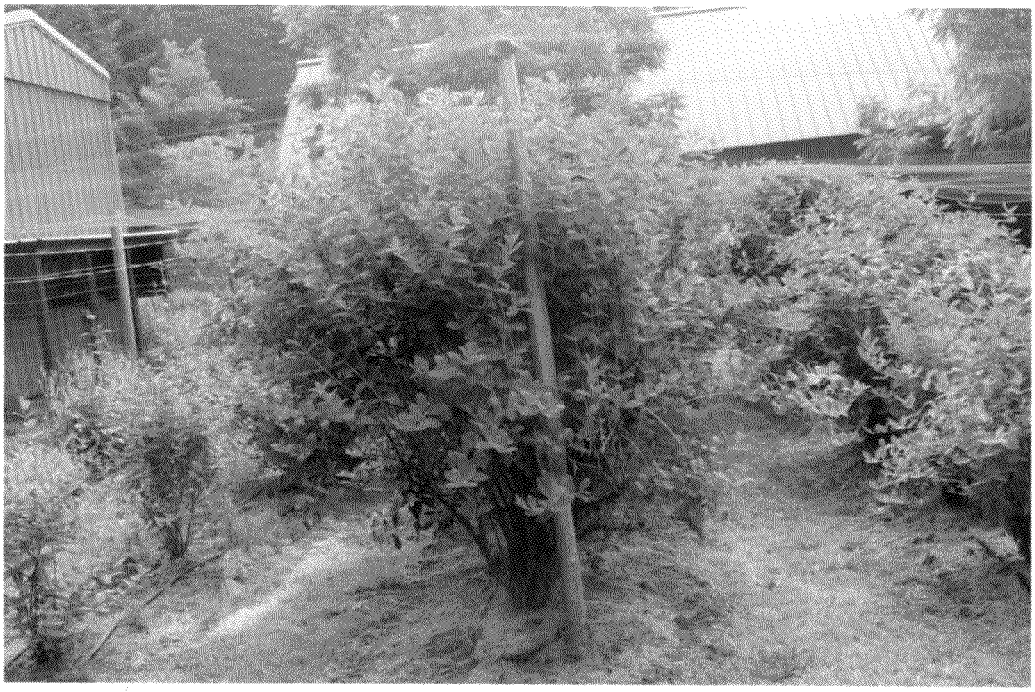
Figure 2:
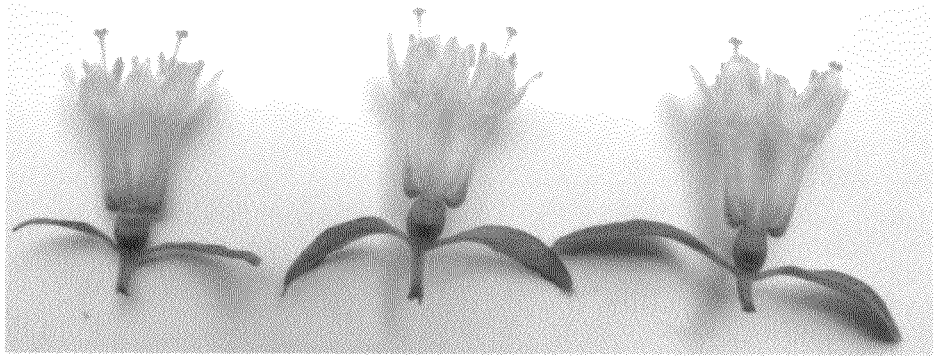

The photograph in FIG. 2 provides a close-up view of the flowers of 'Keiko'.

Figure 3:
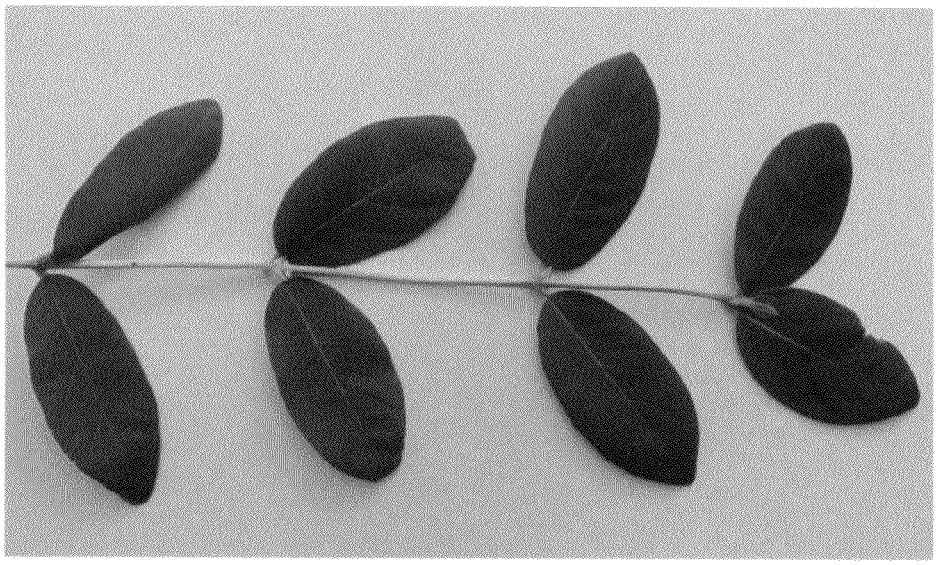

The photograph in FIG. 3 provides a close-up view of the leaves of 'Keiko'.

Figure 4:
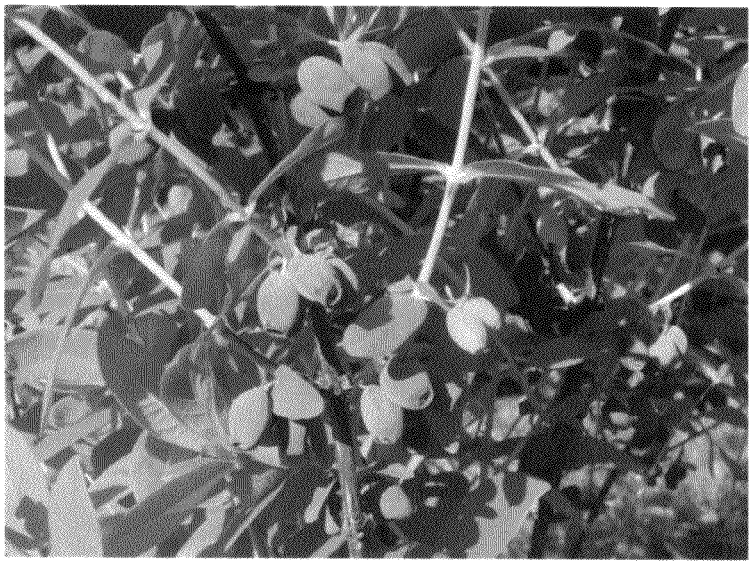

The photograph in FIG. 4 provides a view of the berries of 'Keiko'.

The colors in the photographs may differ slightly from the color values cited in the detailed botanical description, which accurately describe the colors of the new haskap.

DETAILED BOTANICAL DESCRIPTION

The following is a detailed description of 9 year-old plants of the new Japanese haskap as grown on a farm in Corvallis, Oreg. The phenotype of the new cultivar may vary with variations in environmental, climatic, and cultural conditions, as it has not been tested under all possible environmental conditions. The color determination is in accordance with The 1995 R.H.S. Colour Chart of The Royal Horticultural Society, London, England, except where general color terms of ordinary dictionary significance are used.

General description:

*Plant type.*—Deciduous shrub, fruit bearing.

*Plant habit.*—Upright spreading.

*Plant size.*—Up to 2.20 m in height and 1.75 m in width.

*Cold hardiness.*—At least hardy to USDA Zone 7b, has not been tested in colder zones, other plants of the species have been observed to be hardy in U.S.D.A. Zone 2.

*Diseases and pests.*—In some years, minor damage from *Botrytis* sp. has been observed, no significant pests problems have been observed.

*Root description.*—Fibrous.

*Propagation.*—Softwood and hardwood stem cuttings.

*Growth rate.*—Vigorous.

Dormant shoots:

*Density.*—Medium.

*New growth.*—144B in color, and surface glabrous.

*One year-old shoots.*—Average of 45 cm in length and 4 mm in diameter, surface is smooth and glabrous, 176B in color.

*Three year-old shoots.*—95 cm in length, 1.1 cm in diameter (at mid-shoot), 177A in color, surface exfoliating, inner bark 165B in color, outer bark 177D in color.

Foliage description:

*Leaf shape.*—Elliptic.

*Leaf division.*—Simple.

*Leaf base.*—Round.

*Leaf apex.*—Broadly acute.

*Leaf venation.*—Pinnate, upper surface 137A in color, lower surface 138B in color.

*Leaf margins.*—Entire.

*Leaf arrangement.*—Opposite.

*Leaf attachment.*—Petiolate.

*Leaf surface.*—Young leaf upper surface; glabrous, young leaf lower surface; medium amount of pubescence, especially along midrib and lateral veins, mature leaf upper surface; glabrous, mature leaf lower surface; glabrous with slight amount of pubescence on veins.

*Leaf internode length.*—5.3 cm.

*Leaf size.*—Up to 8.5 cm in length and 4 cm in width.

*Leaf color.*—Young leaves upper surface; 144A, young leaves lower surface; 144A, mature leaves upper surface; 137A, mature leaves lower surface; 138B.

*Petioles.*—3 to 4 mm in length and 2 mm in width, 138C in color, glabrous surface.

*Stipules.*—Minute to 5 mm in length and auriculate in shape, glabrous surface.

Inflorescence description:

*Blooming period.*—50% anthesis is on average April 13$^{th}$ in Corvallis, Oreg., blooms approximately 27 days.

*Inflorescence type.*—Small 2-flowered cymule born in leaf axils of lowest 1 to 3 nodes on current years shoot.

*Inflorescence size.*—An average of 2.3 cm in length and 1.4 cm in diameter.

*Flower buds.*—Mixed buds; flower buds are not visible as they are enclosed within the leaves of the bud.

*Flower fragrance.*—None.

*Lastingness of inflorescence.*—7 days.

*Flower type.*—Epigynous.

*Corolla form.*—Funnel-form, narrow at base, widening towards the apex, 5-lobed.

*Flower size.*—2.4 cm in length from base of ovary to tip of stigma, 7 to 8 mm in width at widest part.

*Flower number.*—On 80 shoots there were an average of 3 flowers per shoot.

*Peduncles.*—2 to 7 mm in length, 2 mm in diameter, 136C in color, glabrous surface.

*Pedicels.*—Inconspicuous.

*Bracts.*—2, present at base of ovaries, linear to broadly lanceolate in shape, color 137A on upper surface and 138B on lower surface, glabrous surface, cuspidate apex, cuneate base, 2 to 8 mm in width and 0.8 to 2.5 cm in length.

*Sepals.*—Absent.

*Petals.*—5, fused into tube with apex of each free, 2 to 2.5 mm in diameter at the base, 7 to 8 mm in diameter at apex and 1.6 to 1.7 cm in length, tube portion is an average of 1.4 cm in length and 5 mm in width, free portion is an average of 3 mm in length and 3 mm in width, free petals portions have a rounded apex and entire margins, outer and inner surface of tube and free portions are 11C in color and have a pilose surface.

Reproductive organs:

*Gynoecium.*—1 pistil, an average of 2 cm in length, style 1.9 cm in length with 3 to 4 mm extending beyond corolla, and 1C in color, stigma is about 1.5 mm in diameter and 1C in color, ovary is inferior, oval in shape, 4 to 5 mm in length, 3 mm in diameter and 139C in color.

*Androcoecium.*—5 stamens, about 7 mm in length, adnate to inner surface of corolla tube, filaments are 1C in color and about 7 mm in length, anthers are 18A in color, pollen is very abundant in quantity and 16C in color with 99% acetocarmine stain. Compatibility. — Self-incompatible.

Fruit description:

*Fruit development.*—65 days from mid-bloom to harvest.

*Harvest date.*—Average of June 17$^{th}$ in Corvallis, Oreg.

*Fruit type.*—True berry, consists of 2 ovaries enclosed in fleshy bracts.

*Fruit shape.*—Oval.

*Fruit size.*—(Medium-large), an average of 2.2 cm in length and 1.4 cm in width.

*Fruit surface.*—Smooth with heavy bloom.

*Fruit apex.*—Flattened with a noticeable roll on edges.

*Fruit skin color.*—102A with bloom removed, 106D with bloom.

*Fruit flesh color.*—148C.

*Fruit firmness.*—Medium firm.

*Fruit brix.*—13.5°.

*Fruit juiciness.*—Small amount.

*Fruit taste.*—Sweet and tart.

*Fruit weight.*—An average of 1.6 g (average of 25 berries).

*Peduncle.*—3 to 6 mm in length.

*Pedicel-berry scar.*—Very small, dry.

*Fruit attachment strength.*—Medium; strong enough to avoid pre-harvest drop and loose enough to pick without tearing berry flesh.

*Pre-harvest drop.*—Insignificant.

*Post-harvest.*—Berries maintain their appearance, firmness and taste for at least 4 weeks in cold storage at 33° F. to 35° F.

*Fruit yield.*—7.5 lbs. on a seven year-old plant.

*Market uses.*—Fresh and frozen fruit and particularly suited for processed products.

*Seed.*—Average of 10 seeds per fruit (average of 25 fruits) with a potential of 22, dried seeds; lenticular in shape, dry weight size is 126 mg/100 seeds, 177C in color.

It is claimed:

1. A new and distinct cultivar of Japanese haskap plant named 'Keiko' as herein illustrated and described.

* * * * *